US007375201B2

(12) United States Patent
Miyawaki et al.

(10) Patent No.: US 7,375,201 B2
(45) Date of Patent: May 20, 2008

(54) FLUORESCENT PROTEIN

(75) Inventors: Atsushi Miyawaki, Wako (JP); Ryoko Ando, Asaka (JP); Hidetomo Tanase, Wakayama (JP); Satoshi Karasawa, Tokyo (JP)

(73) Assignees: Riken, Wako-Shi (JP); Medical & Biological Laboratories Co., Ltd., Nagoya-Shi (JP)

(*) Notice: Subject to any disclaimer, the term of this patent is extended or adjusted under 35 U.S.C. 154(b) by 0 days.

(21) Appl. No.: 10/504,325

(22) PCT Filed: Feb. 25, 2003

(86) PCT No.: PCT/JP03/02033

§ 371 (c)(1),
(2), (4) Date: Jul. 12, 2005

(87) PCT Pub. No.: WO03/070952

PCT Pub. Date: Aug. 28, 2003

(65) Prior Publication Data

US 2006/0127877 A1 Jun. 15, 2006

(30) Foreign Application Priority Data

Feb. 25, 2002 (JP) ............................ 2002-047611

(51) Int. Cl.
*C07H 21/04* (2006.01)
*C12N 15/00* (2006.01)
*C12N 5/00* (2006.01)

(52) U.S. Cl. ................. 536/23.1; 536/23.5; 435/320.1; 435/325

(58) Field of Classification Search .................... 435/6, 435/69.1, 320.1, 325; 536/23.5-23.7, 23.1
See application file for complete search history.

(56) References Cited

U.S. PATENT DOCUMENTS

| | | | | |
|---|---|---|---|---|
| 6,933,375 | B2 * | 8/2005 | Falkowski et al. | 536/23.5 |
| 6,969,597 | B2 * | 11/2005 | Lukyanov et al. | 435/69.1 |
| 2003/0017538 | A1 | 1/2003 | Miyawaki et al. | |
| 2005/0032085 | A1 * | 2/2005 | Labas et al. | 435/6 |
| 2005/0090642 | A1 | 4/2005 | Miyawaki et al. | |
| 2005/0106661 | A1 | 5/2005 | Miyawaki et al. | |

FOREIGN PATENT DOCUMENTS

| | | |
|---|---|---|
| EP | 1238982 | 9/2002 |
| JP | 10-234382 | 9/1998 |
| WO | 00/28025 | 5/2000 |
| WO | 00/34320 | 6/2000 |
| WO | 00/34321 | 6/2000 |
| WO | 00/34526 | 6/2000 |
| WO | 01/27150 | 4/2001 |
| WO | 01/57242 | 8/2001 |
| WO | 03/033693 | 4/2003 |
| WO | 03/054191 | 7/2003 |

OTHER PUBLICATIONS

Sergel, T.A., et al. 2000 Journal of Virology 74(11): 5101-5107.*
Yuan, S-M., et al. 1998 Proteins: Structure, Function, and Genetics 30: 136-143.*
R.Y. Tsien et al., Ann. Rev. Biochem., vol. 67, pp. 509-544.
English language Abstract of JP 10-234382, Published Sep. 8, 1998.
M.V. Matz et al., Nat. Biotechnol., vol. 17, No. 10, pp. 969-973, 1999.
K.A. Lukyanov et al., J. Biol. Chem., vol. 275, No. 34, pp. 25879-25882, 2000.
T. Hosaka, Kagaku to Kogyo, vol. 53, No. 5, pp. 612, 2000.
A.F. Fradkov et al., FEBS Letters, vol. 479, No. 3, pp. 127-130, 2000.
A.A. Heikal et al., Proc. Natl. Acad. Sci. USA, vol. 97, No. 22, pp. 11996-12001, 2000.
Oz Reef Press. Resident of the Month, Oz Reef Marine Park, Jun. 1998, retrieved on Mar. 3, 2003 from http://ozreef.org/press/1998/june.html.
Oz Reef Press. Resident of the Month, Oz Reef Marine Park, May 1997, retrieved on Mar. 3, 2003 from http://ozreef.org/press/1997/may.html.
A. Salih et al., Nature, vol. 408, No. 6814, Dec. 14, 2000, pp. 850-853.
N. Gurskaya et al., BMC Biochemistry, vol. 2, No. 6, Jul. 10, 2001, pp. 1-7.
Takeharu Nagai et al., "A Variant of Yellow Fluorescent Protein with fast and Efficient Maturation for Cell-Biological Applications", *Nature Biotechnology*, vol. 20, pp. 87-90 (2002).
Marc-André Elsliger et al., "Structural and Spectral Response of Green Fluorescent Protein Variants to Changes in pH", *Biochemistry*, vol. 38, pp. 5296-5301 (1999).
Kuner, T., and Augustine, G., Neuron vol. 27, pp. 447-459 (2000).
Prasher, D., et al., Gene vol. 111, pp. 229-233 (1992).
Steyer, J., and Almers, W., Nature Reviews Mol. Cell Biol. vol. 2, pp. 268-275 (2001).
Jayaraman, S., et al., J. Biol. Chem. vol. 275, No. 9, pp. 6047-6050 (2000).
Nagai, T., et al., PNAS vol. 98, No. 6, pp. 3197-3202 (2001).
Sawano, A., and Miyawaki, A., Nuc. Acids Res. vol. 28, No. 6.
Reid, B., and Flynn, G., Biochemistry 36, pp. 6786-6791 (1997).

(Continued)

*Primary Examiner*—Maryam Monshipouri
*Assistant Examiner*—Marsha Tsay
(74) *Attorney, Agent, or Firm*—Greenblum & Bernstein, P.L.C.

(57) ABSTRACT

An object of the present invention is to provide a fluorescent protein derived from organisms other than *Aequorea victoria* and having a novel primary structure. According to the present invention, there is provided a fluorescent protein derived from *Halcurias* sp. *L*, which has the following properties:
(1) the excitation maximum wavelength is 494 nm, and the fluorescence maximum wavelength is 506 nm;
(2) the molar absorption coefficient at 494 nm is 94600 $M^{-1}$ $cm^{-1}$;
(3) the quantum yield is 0.65; and
(4) the pH sensitivity of the fluorescent property is low in the range between pH 4 and pH 11.

9 Claims, 6 Drawing Sheets

OTHER PUBLICATIONS

Miyawaki, A., and Tsien, R., Methods in Enzymology vol. 327, pp. 472-500.
Miyawaki, A., et al., PNAS vol. 96, pp. 2135-2140 (1999).
Lang, T., et al., Neuron vol. 18, pp. 857-863 (1997).
Tsuboi, T., et al., Curr. Biol. vol. 10, pp. 1307-1310 (2000).
Angleson, J., and Betz, W., Trends Neurosci. 20, pp. 281-287 (1997).
Miyawaki, A., et al., Nature vol. 388, pp. 882-887 (1997).
Wachter, R., et al., J. Mol. Biol. 301, pp. 157-171 (2000).
Wachter, R., et al., Structure 6, pp. 1267-1277 (1998).
Crameri, A., et al., Nature Biotech. vol. 14, pp. 315-319 (1996).
Heikal, A., et al., PNAS vol. 97, No. 22, pp. 11996-12001 (2000).
Griesbeck, O., et al., J. Biol. Chem. vol. 276, No. 31, pp. 29188-29194 (2001).
Pouli, A., et al., Biochem J. 331, pp. 669-675 (1998).
Cadwell, R., and Joyce, G., PCR Methods and Applications 3, pp. S136-S140 (1994).
DOPF et al., Gene, vol. 173, pp. 39-44 (1996).
F. Yang et al., Nature Biology, 1996, vol. 14, pp. 1246-1251.
Database UnitProt, Dec. 1, 2001, XP002342731, Database accession No. Q963F5.
Database EMBL, Jun. 18, 2001, XP002342732, Database accession No. AF384683.

* cited by examiner

FLUORESCENT PROTEIN

CROSS-REFERENCE TO RELATED APPLICATIONS

This application is a 371 of PCT/JP03/02033, filed on Feb. 25, 2003, which claims priority to Japenese Patent Application No. 2002-47611 filed on Feb. 25, 2002, each of which is incorporated herein by reference.

TECHNICAL FIELD

The present invention relates to a novel fluorescent protein. More specifically, the present invention relates to a novel fluorescent protein derived from *Halcurias* sp. *L*, and the use thereof.

BACKGROUND ART

Green fluorescent protein (GFP) derived from *Aequorea victoria*, a jellyfish, has many purposes in biological systems. Recently, various GFP mutants have been produced based on the random mutagenesis and semi-rational mutagenesis, wherein a color is changed, a folding property is improved, luminance is enhanced, or pH sensitivity is modified. Fluorescent proteins such as GFP are fused with other proteins by gene recombinant technique, and monitoring of the expression and transportation of the fusion proteins is carried out.

One of the most commonly used types of GFP mutant is Yellow fluorescent protein (YFP). Among *Aequorea*-derived GFP mutants, YFP exhibits the fluorescence with the longest wavelength. The values $\epsilon$ and $\Phi$ of the majority of YEPs are 60,000 to 100,000 $M^{-1}$ $cm^{-1}$ and 0.6 to 0.8, respectively (Tsien, R. Y. (1998). Ann. Rev. Biochem. 67, 509-544). These values are comparable to those of the general fluorescent group (fluorescein, rhodamine, etc.). Accordingly, improvement of the absolute luminance of YFP is nearly approaching its limit.

DISCLOSURE OF THE INVENTION

An object of the present invention is to provide a fluorescent protein derived from organisms other than *Aequorea victoria* and having a novel primary structure.

In order to achieve the above object, the present inventors have conducted intensive studies. The present inventors have focused on *Halcurias* sp. *L* as a living organism showing fluorescence, and performed expression cloning by using cDNA library derived from *Halcurias* sp. *L*. As a result, they have succeeded in cloning a gene encoding a novel fluorescent protein. The present inventors have examined the fluorescent properties of the obtained fluorescent protein, and as a result, they have found that this fluorescent protein has desired fluorescent properties. Further, the present inventors have produced mutant proteins by introducing mutations in the amino acid sequence of the fluorescent protein, and have examined the fluorescent properties. As a result, they have succeeded in obtaining fluorescent proteins having improved fluorescent properties. The present invention has been completed based on these findings.

Thus, the present invention provides a fluorescent protein derived from *Halcurias* sp. *L*, which has the following properties:

(1) the excitation maximum wavelength is 494 nm, and the fluorescence maximum wavelength is 506 nm;

(2) the molar absorption coefficient at 494 nm is 94600 $M^{-1}$ $cm^{-1}$;

(3) the quantum yield is 0.65; and (4) the pH sensitivity of the fluorescent property is low in the range between pH 4 and pH 11.

In another aspect of the present invention, there is provided a mutant protein of the above fluorescent protein, which has the following properties:

(1) the excitation maximum wavelength is 494 nm, and the fluorescence maximum wavelength is 507 nm;

(2) the molar absorption coefficient at 494 nm is 68800 $M^{-1}$ $cm^{-1}$;

(3) the quantum yield is 0.66; and (4) the pH sensitivity of the fluorescent property is low in the range between pH 6 and pH 11.

In further another aspect of the present invention, there is provided a mutant protein of the above fluorescent protein, which has the following properties:

(1) the excitation maximum wavelength is 507 nm, and the fluorescence maximum wavelength is 514 nm;

(2) the molar absorption coefficient at 507 nm is 88600 $M^{-1}$ $cm^{-1}$;

(3) the quantum yield is 0.61; and (4) the pH sensitivity of the fluorescent property is low in the range between pH 9 and pH 11.

In further another aspect of the present invention, there is provided a mutant protein of the above fluorescent protein, which has the following properties:

(1) the excitation maximum wavelength is 391 nm, and the fluorescence maximum wavelength is 505 nm;

(2) the molar absorption coefficient at 391 nm is 20000 $M^{-1}$ $cm^{-1}$;

(3) the quantum yield is 0.84; and (4) the pH sensitivity of the fluorescent property is low in the range between pH 4 and pH 10.

In further another aspect of the present invention, there is provided a fluorescent protein having either one of the following amino acid sequences:

(a) an amino acid sequence shown in SEQ ID NO: 1; or (b) an amino acid sequence comprising a deletion, substitution and/or addition of one or several amino acids with respect to the amino acid sequence shown in SEQ ID NO: 1, and having fluorescent properties.

In further another aspect of the present invention, there is provided a fluorescent protein having either one of the following amino acid sequences:

(a) an amino acid sequence shown in SEQ ID NO: 3; or (b) an amino acid sequence comprising a deletion, substitution and/or addition of one or several amino acids with respect to the amino acid sequence shown in SEQ ID NO: 3, and having fluorescent properties.

In further another aspect of the present invention, there is provided a fluorescent protein having either one of the following amino acid sequences:

(a) an amino acid sequence shown in SEQ ID NO: 5; or (b) an amino acid sequence comprising a deletion, substitution and/or addition of one or several amino acids with respect to the amino acid sequence shown in SEQ ID NO: 5, and having fluorescent properties.

In further another aspect of the present invention, there is provided a fluorescent protein having either one of the following amino acid sequences:

(a) an amino acid sequence shown in SEQ ID NO: 7; or (b) an amino acid sequence comprising a deletion, substitution and/or addition of one or several amino acids with respect to the amino acid sequence shown in SEQ ID NO: 7, and having fluorescent properties.

In further another aspect of the present invention, there is provided DNA of either one of the following:

(a) DNA which encodes the amino acid sequence shown in SEQ ID NO: 1;

(b) DNA which encodes an amino acid sequence comprising a deletion, substitution and/or addition of one or several amino acids with respect to the amino acid sequence shown in SEQ ID NO: 1, and encodes a fluorescent protein.

(c) DNA having a nucleotide sequence shown in SEQ ID NO: 2; or (d) DNA having a nucleotide sequence comprising a deletion, substitution and/or addition of one or several nucleotides with respect of the nucleotide sequence shown in SEQ ID NO: 2, and encoding a fluorescent protein.

In further another aspect of the present invention, there is provided DNA of either one of the following:

(a) DNA which encodes the amino acid sequence shown in SEQ ID NO: 3;

(b) DNA which encodes an amino acid sequence comprising a deletion, substitution and/or addition of one or several amino acids with respect to the amino acid sequence shown in SEQ ID NO: 3, and encodes a fluorescent protein.

(c) DNA having a nucleotide sequence shown in SEQ ID NO: 4; or (d) DNA having a nucleotide sequence comprising a deletion, substitution and/or addition of one or several nucleotides with respect of the nucleotide sequence shown in SEQ ID NO: 4, and encoding a fluorescent protein.

In further another aspect of the present invention, there is provided DNA of either one of the following:

(a) DNA which encodes the amino acid sequence shown in SEQ ID NO: 5;

(b) DNA which encodes an amino acid sequence comprising a deletion, substitution and/or addition of one or several amino acids with respect to the amino acid sequence shown in SEQ ID NO: 5, and encodes a fluorescent protein.

(c) DNA having a nucleotide sequence shown in SEQ ID NO: 6; or (d) DNA having a nucleotide sequence comprising a deletion, substitution and/or addition of one or several nucleotides with respect of the nucleotide sequence shown in SEQ ID NO: 6, and encoding a fluorescent protein.

In further another aspect of the present invention, there is provided DNA of either one of the following:

(a) DNA which encodes the amino acid sequence shown in SEQ ID NO: 7;

(b) DNA which encodes an amino acid sequence comprising a deletion, substitution and/or addition of one or several amino acids with respect to the amino acid sequence shown in SEQ ID NO: 7, and encodes a fluorescent protein.

(c) DNA having a nucleotide sequence shown in SEQ ID NO: 8; or (d) DNA having a nucleotide sequence comprising a deletion, substitution and/or addition of one or several nucleotides with respect of the nucleotide sequence shown in SEQ ID NO: 8, and encoding a fluorescent protein.

In another aspect of the present invention, there is provided a recombinant vector having any of the above-described DNAs.

In another aspect of the present invention, there is provided a transformant having any of the above-described DNAs or recombinant vector.

In another aspect of the present invention, there is provided a fusion fluorescent protein consisting of any of the above-described fluorescent proteins and another protein. Preferably, said another protein is one that localizes in the cell, and more preferably one specific to an intracellular organella.

In another aspect of the present invention, there is provided a method for analyzing the localization or dynamics of a protein in cells, characterized in that any of the above-described fusion protein is allowed to be expressed in cells.

In another aspect of the present invention, there is provided a fluorescent reagent kit which comprises any of the above-described fluorescent proteins, DNAs, recombinant vector, transformant or fusion protein.

BEST MODE FOR CARRYING OUT THE INVENTION

Figure 1:
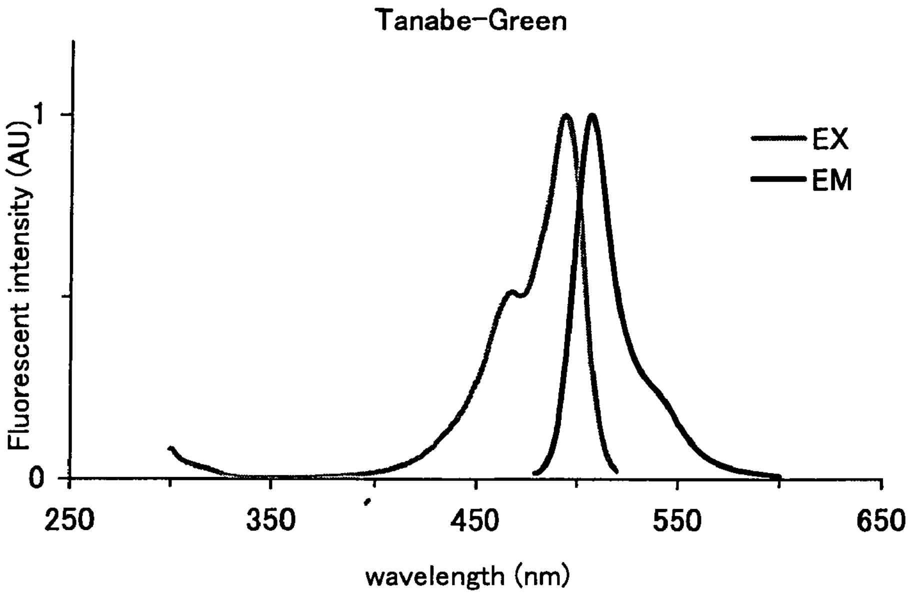
FIG. 1 shows excitation and fluorescence spectra of Tanabe-Green.

The embodiments of the present invention will be described in detail below.

(1) Fluorescent Protein of the Present Invention

The fluorescent protein of the present invention is characterized in that it is derived from *Halcurias* sp. *L* and has the following properties:

(1) the excitation maximum wavelength is 494 nm, and the fluorescence maximum wavelength is 506 nm;

(2) the molar absorption coefficient at 494 nm is 94600 $M^{-1}cm^{-1}$;

(3) the quantum yield is 0.65; and (4) the pH sensitivity of the fluorescent property is low in the range between pH 4 and pH 11.

*Halcurias* sp. *L* is one type of sea anemones, and is characterized in that it shows fluorescence. In Examples of the present specification described later, the fluorescent protein of the present invention having the above properties was isolated by using *Halcurias* sp. *L* harvested in seaward of Tanabe-shi, Wakayama-prefecture as a starting material. However, in some cases, the fluorescent protein of the present invention can be obtained also from sea anemones which emit fluorescence other than *Halcurias* sp. *L*. Such fluorescent proteins are also included in the scope of the present invention.

As described in Examples mentioned later, the fluorescent protein of the present invention has an excitation maximum wavelength of 494 nm and a fluorescence maximum wavelength of 506 nm. It has a molar absorption coefficient of 94600 $M^{-1}cm^{-1}$ at 494 nm, and a quantum yield of 0.65.

In contrast, EGFP (Clontech) has a molar absorption coefficient of 44,800 and a quantum yield of 0.600. Molar absorption coefficient represents the amount of photons absorbed per mole of fluorescent molecules. Quantum yield is a value showing what amount of the absorbed photons can be emitted as a fluorescence. Accordingly, the increased values of the molar absorption coefficient and quantum yield indicate that fluorescence is strong. Therefore, the fluorescent protein of the present invention, whose molar absorption coefficient and quantum yield are greater than those of EGFP, emits a fluorescence which is stronger than that of EGFP.

The fluorescent protein of the present invention is characterized in that the pH sensitivity of the fluorescent properties is low in the range between pH 4 and pH 11. This is to say, a fluctuation in the peak value of fluorescence intensity is small in the range between pH 4 and pH 11, and thus, high fluorescence intensity can be maintained in this pH range. In the case of the conventionally used EGFP, since fluorescence intensity decreases at pH 7 or less, limitation is put on its use in vivo. However, the fluorescent protein of the present invention is free from such limitation.

The molecular weight of the fluorescent protein of the present invention is about 28 kDa.

Further, the present invention provides a mutant protein (hereinafter referred to as Mutant 1) of the above fluorescent protein, which has the following properties:

(1) the excitation maximum wavelength is 494 nm, and the fluorescence maximum wavelength is 507 nm;
(2) the molar absorption coefficient at 494 nm is 68800 $M^{-1}$ $cm^{-1}$;
(3) the quantum yield is 0.66; and
(4) the pH sensitivity of the fluorescent property is low in the range between pH 6 and pH 11.

Further, the present invention provides a mutant protein (hereinafter referred to as Mutant 2) of the above fluorescent protein, which has the following properties:

(1) the excitation maximum wavelength is 507 nm, and the fluorescence maximum wavelength is 514 nm;
(2) the molar absorption coefficient at 507 nm is 88600 $M^{-1}$ $cm^{-1}$;
(3) the quantum yield is 0.61; and
(4) the pH sensitivity of the fluorescent property is low in the range between pH 9 and pH 11.

Further, the present invention provides a mutant protein (hereinafter referred to as Mutant 3) of the above fluorescent protein, which has the following properties:

(1) the excitation maximum wavelength is 391 nm, and the fluorescence maximum wavelength is 505 nm;
(2) the molar absorption coefficient at 391 nm is 20000 $M^{-1}$ $cm^{-1}$;
(3) the quantum yield is 0.84; and
(4) the pH sensitivity of the fluorescent property is low in the range between pH 4 and pH 10.

These Mutants 1, 2, and 3 were obtained by using the gene encoding the aforementioned fluorescent protein of the present invention as a template and performing PCR in a state where $MnCl_2$ was added, so as to randomly introduce mutations therein.

Mutant 1 is one whose illuminating and agglutinating properties are reduced. Mutant 2 is characterized in that the peak of a fluorescence spectrum is shifted to a long wavelength and in that its pH sensitivity is increased. Mutant 3 is a mutant characterized in that the peak of the excitation spectrum is shifted to a short wavelength. In addition, since Mutants 1 and 2 have a molar absorption coefficient and a quantum yield that are greater than those of EGFP, these Mutants 1 and 2 emit stronger fluorescence than that of EGFP. The molecular weight of Mutants 1, 2 and 3 is about 28 kDa.

The term "the fluorescent protein of the present invention" used herein covers all of the fluorescent proteins within the scope of the present invention, which include the aforementioned Mutants 1, 2 and 3.

The examples of the fluorescent protein of the present invention include a fluorescent protein having either one of the following amino acid sequences:

(a) an amino acid sequence shown in SEQ ID NO: 1; or
(b) an amino acid sequence comprising a deletion, substitution and/or addition of one or several amino acids with respect to the amino acid sequence shown in SEQ ID NO: 1, and having fluorescent properties which are equivalent to those of a protein having an amino acid sequence shown in SEQ ID NO: 1.

The examples of the Mutant 1 include a fluorescent protein having either one of the following amino acid sequences:

(a) an amino acid sequence shown in SEQ ID NO: 3; or
(b) an amino acid sequence comprising a deletion, substitution and/or addition of one or several amino acids with respect to the amino acid sequence shown in SEQ ID NO: 3, and having fluorescent properties.

The examples of the Mutant 2 include a fluorescent protein having either one of the following amino acid sequences:

(a) an amino acid sequence shown in SEQ ID NO: 5; or
(b) an amino acid sequence comprising a deletion, substitution and/or addition of one or several amino acids with respect to the amino acid sequence shown in SEQ ID NO: 5, and having fluorescent properties.

The examples of the Mutant 3 include a fluorescent protein having either one of the following amino acid sequences:

(a) an amino acid sequence shown in SEQ ID NO: 7; or
(b) an amino acid sequence comprising a deletion, substitution and/or addition of one or several amino acids with respect to the amino acid sequence shown in SEQ ID NO: 7, and having fluorescent properties.

The scope of "one or several" in the phrase "an amino acid sequence comprising a deletion, substitution and/or addition of one or several amino acids" is not particularly limited in the present specification. For example, it means 1 to 20, preferably 1 to 10, more preferably 1 to 7, further preferably 1 to 5, and particularly preferably 1 to 3.

The term "having fluorescent properties" covers all of the cases where any fluorescence is given. Various properties such as fluorescence intensity, excitation wavelength, fluorescence wavelength or pH sensitivity, may be changed or may remain unchanged.

The method of obtaining the fluorescent protein of the present invention is not particularly limited. The protein may be either a protein synthesized by chemosynthesis, or recombinant protein produced by a gene recombination technique.

Where a recombinant protein is produced, it is necessary to obtain DNA encoding the protein. Appropriate primers are designed by using information regarding the amino acid sequence shown in SEQ ID NOS: 1, 3, 5 or 7 of the sequence listing of the present specification and the nucleotide sequence shown in SEQ ID NOS: 2, 4, 6 or 8 thereof. Using these primers, PCR is carried out by using cDNA clones of the above-described various types of known fluorescent proteins as a template, so that DNA encoding the fluorescent protein of the present invention can be obtained. Where a partial fragment of DNA encoding the fluorescent protein of the present invention are obtained by the above-described PCR, the produced DNA fragments are ligated to one another by a gene recombination technique, so that DNA encoding the desired fluorescent protein can be obtained. The fluorescent protein of the present invention can be produced by introducing this DNA into an appropriate expression system. Expression in an expression system will be described later in the present specification.

(2) DNA of the Present Invention

According to the present invention, a gene encoding the fluorescent protein of the present invention is provided.

Specific examples of DNA encoding the fluorescent protein (including Mutants 1, 2 and 3) of the present invention may include either one of the following DNAs:

(a) DNA which encodes the amino acid sequence shown in SEQ ID NO: 1, 3, 5 or 7;

(b) DNA which encodes an amino acid sequence comprising a deletion, substitution and/or addition of one or several amino acids with respect to the amino acid sequence shown in SEQ ID NO: 1, 3, 5 or 7, and encodes a fluorescent protein.

(c) DNA having a nucleotide sequence shown in SEQ ID NO: 2, 4, 6 or 8; or (d) DNA having a nucleotide sequence comprising a deletion, substitution and/or addition of one or several nucleotides with respect of the nucleotide sequence shown in SEQ ID NO: 2, 4, 6 or 8, and encoding a fluorescent protein.

The DNA of the present invention can be synthesized by, for example, the phosphoamidite method, or it can also be produced by polymerase chain reaction (PCR) using specific primers. The DNA of the present invention or a fragment thereof is produced by the method described above in the specification.

A method of introducing a desired mutation into a certain nucleic acid sequence is known to a person skilled in the art. For example, known techniques such as a site-directed mutagenesis, PCR using degenerated oligonucleotides, or the exposure of cells containing nucleic acid to mutagens or radioactive rays, are appropriately used, so as to construct DNA having a mutation. Such known techniques are described in, for example, Molecular Cloning: A Laboratory Manual, $2^{nd}$ Ed., Cold Spring Harbor Laboratory, Cold Spring Harbor, N.Y., 1989; and Current Protocols in Molecular Biology, Supplements 1 to 38, John Wiley & Sons (1987-1997).

(3) Recombinant Vector of the Present Invention

The DNA of the present invention can be inserted into a suitable vector and used. The type of a vector used in the present invention is not particularly limited. For example, it may be either a vector that can autonomously replicate (e.g., a plasmid, etc.), or vector that is incorporated into the genomes of host cells when it is introduced into the host cells and is then replicated together with the chromosome into which it is incorporated.

The vector used in the present invention is preferably an expression vector. In an expression vector, elements necessary for transcription (e.g., a promoter, etc.) are functionally ligated to the DNA of the present invention. The promoter is a DNA sequence which shows a transcriptional activity in host cells, and it is appropriately selected depending on the type of host cells.

Examples of a promoter which can operate in bacterial cells may include a *Bacillus stearothermophilus* maltogenic amylase gene promoter, a *Bacillus licheniformis* alpha-amylase gene promoter, a *Bacillus amyloliquefaciens* BAN amylase gene promoter, a *Bacillus subtilis* alkaline protease gene promoter, a *Bacillus pumilus* xylosidase gene promoter, $P_R$ and $P_L$ promoters of phage rhamda, and lac, trp and tac promoters of *Escherichia coli*.

Examples of a promoter which can operate in mammalian cells may include an SV40 promoter, an MT-1 (metallothionein gene) promoter, and an adenovirus-2 major late promoter. Examples of a promoter which can operate in insect cells may include a polyhedrin promoter, a P10 promoter, an *Autographa californica* polyhedrosis basic protein promoter, a baculovirus immediate-early gene 1 promoter, and a baculovirus 39K delayed-early gene promoter. Examples of a promoter which can be operate in yeast host cells may include promoters derived from yeast glycolytic genes, an alcohol dehydrogenase gene promoter, a TPI1 promoter, and an ADH2-4c promoter.

Examples of a promoter which can operate in filamentous cells may include an ADH3 promoter and a tpiA promoter.

In addition, an appropriate terminator such as a human growth hormone terminator, or a TPI1 terminator or ADH3 terminator for fungal cells, may be functionally bound to the DNA of the present invention, as necessary. The recombinant vector of the present invention may further have elements such as a polyadenylation signal (e.g., one derived from SV40 or the adenovirus 5E1b region), a transcription enhancer sequence (e.g., an SV40 enhancer), or a translation enhancer sequence (e.g., one encoding the adenovirus VA RNA).

The recombinant vector of the present invention may further comprise a DNA sequence which enables the replication of the recombinant vector in host cells. SV40 replication origin is an example of such a sequence (when the host cells are mammalian cells).

The recombinant vector of the present invention may further comprise a selective marker. Examples of such a selective marker may include genes, complements of which are absent from host cells, such as a dihydrofolate reductase (DHFR) gene or a *Shizosaccharomyces pombe* TPI gene, and drug resistant genes such as ampicillin, kanamycin, tetracycline, chloramphenicol, neomycin or hygromycin-resistant genes.

A method for ligating the DNA of the present invention, a promoter and, as desired, a terminator and/or a secretory signal sequence to one another and inserting these items into a suitable vector is known to a person skilled in the art.

(4) Transformant of the Present Invention

A transformant can be produced by introducing the DNA or recombinant vector of the present invention into a suitable host.

Any cell can be used as a host cell into which the DNA or recombinant vector of the present invention is introduced, as long as the DNA construct of the present invention can be expressed therein. Examples of such a cell may include bacteria, yeasts, fungal cells, and higher eukaryotic cells.

Examples of bacteria may include Gram-positive bacteria such as *Bacillus* or *Streptomyces*, and Gram-negative bacteria such as *Escherichia coli*. These bacteria may be transformed by the protoplast method or other known methods, using competent cells.

Examples of mammalian cells may include HEK 293 cells, HeLa cells, COS cells, BHK cells, CHL cells, and CHO cells. A method of transforming mammalian cells and expressing the introduced DNA sequence in the cells is also known. Examples of such a method may include the electroporation, the calcium phosphate method, and the lipofection method.

Examples of yeast cells may include those belonging to *Saccharomyces* or *Shizosaccharomyces*. Examples of such cells may include *Saccharomyces cerevisiae* and *Saccharomyces kluyveri*. Examples of a method of introducing a recombinant vector into yeast host cells may include the electroporation, the spheroplast method, and the lithium acetate method.

Examples of other fungal cells may include those belonging to *Filamentous fungi* such as *Aspergillus, Neurospora, Fusarium* or *Trichoderma*. Where *Filamentous fungi* are used as host cells, transformation can be carried out by incorporating DNA constructs into host chromosomes, so as to obtain recombinant host cells. Incorporation of DNA constructs into the host chromosomes is carried out by known methods, and such known methods may include homologous recombination and heterologous recombination.

Where insect cells are used as host cells, both a vector into which a recombinant gene is introduced and a baculovirus are co-introduced into insect cells, and a recombinant virus is obtained in the culture supernatant of the insect cells. Thereafter, insect cells are infected with the recombinant virus, so as to allow the cells to express proteins (described in, for example, Baculovirus Expression Vectors, A Laboratory Manual; and Current Protocols in Molecular Biology, Bio/Technology, 6, 47 (1988)).

The *Autographa californica* nuclear polyhedrosis virus, which is a virus infecting to insects belonging to *Barathra brassicae*, can be used as baculovirus.

Examples of insect cells used herein may include Sf9 and Sf21, which are *Spodoptera frugiperda* ovarian cells [Baculovirus Expression Vectors, A Laboratory Manual, W. H. Freeman & Company, New York, (1992)], and HiFive (manufactured by Invitrogen), which are *Trichoplusia ni* ovarian cells.

Examples of the method of co-introducing both a vector into which a recombinant gene has been introduced and the above baculovirus into insect cells to prepare a recombinant virus may include the calcium phosphate method and the lipofection method.

The above transformant is cultured in an appropriate nutritive medium under conditions enabling the introduced DNA construct to be expressed. In order to isolate and purify the fusion fluorescent protein of the present invention from the culture product of the transformant, common methods of isolating and purifying proteins may be used.

For example, where the protein of the present invention is expressed in a state dissolved in cells, after completion of the culture, cells are recovered by centrifugal separation, and the recovered cells are suspended in a water type buffer. Thereafter, the cells are disintegrated using an ultrasonic disintegrator or the like, so as to obtain a cell-free extract. A supernatant is obtained by centrifuging the cell-free extract, and then, a purified sample can be obtained from the supernatant by applying, singly or in combination, the following ordinary protein isolation and purification methods: the solvent extraction, the salting-out method using ammonium sulfate or the like, the desalting method, the precipitation method using an organic solvent, the anion exchange chromatography using resins such as diethylaminoethyl (DEAE) sepharose, the cation exchange chromatography using resins such as S-Sepharose FF (manufactured by Pharmacia), the hydrophobic chromatography using resins such as butyl sepharose or phenyl sepharose, the gel filtration method using a molecular sieve, the affinity chromatography, the chromatofocusing method, and the electrophoresis such as isoelectric focusing.

(5) Use of the Fluorescent Protein of the Present Invention and a Fusion Fluorescent Protein Comprising the Same The fluorescent protein of the present invention can be fused with another protein, so as to construct a fusion fluorescent protein.

A method of obtaining the fusion fluorescent protein of the present invention is not particularly limited. It may be either a protein synthesized by chemosynthesis, or recombinant protein produced by a gene recombination technique.

Where a recombinant protein is produced, it is necessary to obtain DNA encoding the protein. Appropriate primers are designed using the information regarding the amino acid sequence shown in SEQ ID NO: 1, 3, 5 or 7 of the sequence listing of the present specification and the nucleotide sequence shown in SEQ ID NO: 2, 4, 6 or 8 thereof. Using these primers, PCR is carried out using a DNA fragment containing the gene of the fluorescent protein of the present invention as a template, so as to produce DNA fragments necessary for construction of the DNA encoding the fluorescent protein of the present invention. Moreover, DNA fragments encoding a protein to be fused is also obtained in the same above manner.

Subsequently, the thus obtained DNA fragments are ligated to one another by a gene recombination technique, so that DNA encoding the desired fusion fluorescent protein can be obtained. This DNA is then introduced into an appropriate expression system, so that the fusion fluorescent protein of the present invention can be produced.

The fluorescent protein of the present invention has an extremely high utility value as a marker. This is to say, the fluorescent protein of the present invention is purified as a fusion protein with an amino acid sequence to be tested, and the fusion protein is introduced into cells by methods such as the microinjection. By observing the distribution of the fusion protein over time, targeting activity of the amino acid sequence to be tested can be detected in the cells.

The type of another protein (an amino acid sequence to be tested) with which the fluorescent protein of the present invention is fused is not particularly limited. Preferred examples may include proteins localizing in cells, proteins specific for intracellular organelles, and targeting signals (e.g., a nuclear transport signal, a mitochondrial presequence, etc.). In addition, the fluorescent protein of the present invention can be expressed in cells and used, as well as being introduced into cells by the microinjection or the like. In this case, a vector into which the DNA encoding the fluorescent protein of the present invention is inserted in such a way that it can be expressed, is introduced into host cells.

Moreover, the fluorescent protein of the present invention can also be used as a reporter protein to determine promoter activity. This is to say, a vector is constructed such that DNA encoding the fluorescent protein of the present invention is located downstream of a promoter to be tested, and the vector is then introduced into host cells. By detecting the fluorescence of the fluorescent protein of the present invention which is emitted from the cells, the activity of the promoter to be tested can be determined. The type of a promoter to be tested is not particularly limited, as long as it operates in host cells.

A vector used to detect the targeting activity of the above amino acid sequence to be tested or to determine promoter activity is not particularly limited. Examples of a vector preferably used for animal cells may include pNEO (P. Southern, and P. Berg (1982) J. Mol. Appl. Genet. 1: 327), pCAGGS (H. Niwa, K. Yamamura, and J. Miyazaki, Gene 108, 193-200 (1991)), pRc/CMV (manufactured by Invitrogen), and pCDM8 (manufactured by Invitrogen). Examples of a vector preferably used for yeasts may include pRS303, pRS304, pRS305, pRS306, pRS313, pRS314, pRS315, pRS316 (R. S. Sikorski and P. Hieter (1989) Genetics 122: 19-27), pRS423, pRS424, pRS425, pRS426 (T. W. Christianson, R. S. Sikorski, M. Dante, J. H. Shero, and P. Hieter (1992) Gene 110: 119-122).

In addition, the type of cells used herein is also not particularly limited. Various types of animal cells such as L cells, BalbC-3T3 cells, NIH3T3 cells, CHO (Chinese hamster ovary) cells, HeLa cells or NRK (normal rat kidney) cells, yeast cells such as *Saccharomyces cerevisiae, Escherichia coli* cells, or the like can be used. Vector can be introduced into host cells by common methods such as the calcium phosphate method or the electroporation.

The above obtained fusion fluorescent protein of the present invention wherein the fluorescent protein of the present invention is fused with another protein (referred to as a protein X) is allowed to be expressed in cells. By monitoring a fluorescence emitted, it becomes possible to analyze the localization or dynamics of the protein X in cells. That is, cells transformed or transfected with DNA encoding the fusion fluorescent protein of the present invention are observed with a fluorescence microscope, so that the localization and dynamics of the protein X in the cells can be visualized and thus analyzed.

For example, by using a protein specific for an intracellular organella as a protein X, the distribution and movement of a nucleus, a mitochondria, an endoplasmic reticulum, a Golgi body, a secretory vesicle, a peroxisome, etc., can be observed.

Moreover, for example, axis cylinders or dendrites of the nerve cells show an extremely complicated change in strikes in an individual who is under development. Accordingly, fluorescent labeling of these sites enables a dynamic analysis.

The fluorescence of the fluorescent protein of the present invention can be detected with a viable cell. Such detection can be carried out using, for example, a fluorescence microscope (Axiophoto Filter Set 09 manufactured by Carl Zeiss) or an image analyzer (Digital Image Analyzer manufactured by ATTO).

The type of a microscope can be appropriately selected depending on purposes. Where frequent observation such as pursuit of a change over time is carried out, an ordinary incident-light fluorescence microscope is preferable. Where observation is carried out while resolution is emphasized, for example, in the case of searching localization in cells specifically, a confocal laser scanning microscope is preferable. In terms of maintenance of the physiological state of cells and prevention from contamination, an inverted microscope is preferable as a microscope system. When an erecting microscope with a high-powered lens is used, a water immersion lens can be used.

A filter set can be appropriately selected depending on the fluorescence wavelength of a fluorescent protein. In the case of the fluorescent protein having the excitation maximum wavelength of 494 nm and the fluorescence maximum wavelength of 506 nm or 507 nm among the fluorescent protein of the present invention, a filter having an excitation light between approximately 480 and 500 nm and a fluorescence between approximately 500 and 540 nm can be preferably used. Further, in the case of the fluorescent protein having the excitation maximum wavelength of 507 nm and the fluorescence maximum wavelength of 514 nm among the fluorescent protein of the present invention, a filter having an excitation light between approximately 490 and 510 nm and a fluorescence between approximately 510 and 550 nm can be preferably used. Further, in the case of the fluorescent protein having the excitation maximum wavelength of 391 nm and the fluorescence maximum wavelength of 505 nm among the fluorescent protein of the present invention, a filter having an excitation light between approximately 380 and 400 nm and a fluorescence between approximately 480 and 530 nm can be preferably used.

When viable cells are observed over time using a fluorescence microscope, a high sensitive cooled CCD camera is used, since photography is carried out in a short time. In the case of the cooled CCD camera, CCD is cooled to decrease thermal noise, so that a weak fluorescence image can be clearly photographed by exposure in a short time.

(6) Kit of the Present Invention

The present invention provides a kit for analyzing the localization of intracellular components and/or analyzing physiologically active substances, which is characterized in that it comprises at least one selected from the fluorescent protein, the fusion fluorescent protein, the DNA, the recombinant vector, or the transformant, which are described in the present specification. The kit of the present invention can be produced from commonly used materials that are known per se, by using common methods.

Reagents such as the fluorescent protein or the DNA are dissolved in an appropriate solvent, so that the reagents can be prepared in a form suitable for conservation. Water, ethanol, various types of buffer solution, etc. can be used as such a solvent.

The present invention will be further described in the following examples. However, the present invention is not limited by these examples.

EXAMPLES

Example 1

Isolation of Fluorescent Protein Gene (Tanabe-Green) from Sea Anemone

A fluorescent protein gene was isolated from *Halcurias* sp. *L* emitting fluorescence (which can be found at a depth of 40 meters off the coast of Tanabe-shi, Wakayama prefecture, Japan) by the following procedures.

(1) Extraction of Total RNA

Total RNA was extracted by acidic guanidium/phenol/chloroform method. Frozen *Halcurias* sp. *L* was crushed in a mortar, and then, using a homogenizer, the crushed *Halcurias* sp. *L* was homogenized in a denaturation solution. Thereafter, phenol/chloroform was added thereto, followed by centrifugation to separate RNA from protein and DNA. A water phase containing RNA was added to isopropanol, and the mixture was centrifuged, so as to obtain total RNA as a precipitate.

(2) Purification of RNA

Using Oligotex-dT30 (manufactured by Roche), mRNA was separated from the total RNA.

Oligotex-dT30<super> was added to the total RNA, and the mixture was then heated, so as to destroy the secondary structure of the RNA. Thereafter, the RNA was bound to Oligotex-dT at 37° C. After washing, the resultant product was heated and centrifuged, so as to obtain a supernatant eluted from the mRNA. Oligotex-dt was eliminated from the supernatant, and then, mRNA was allowed be precipitated with ethanol and NaCl. The mRNA was then dissolved in water.

(3) Preparation of cDNA

A cDNA fragment was prepared using TimeSaver and Directional Cloning Toolbox (both of which were manufactured by Amersham Pharmacia).

The mRNA was heated to destroy the secondary structure thereof. Thereafter, the mRNA, DTT, and a NotI-dT primer were added to First-Strand Reaction Mix, so as to synthesize a first strand. This was then added to Second-Strand Reaction Mix, so as to synthesize a second strand. The synthesized second strand was purified with a span column attached with the kit. EcoRI adaptors were added to both termini of the purified double-stranded cDNA, and only the 3'-side thereof was cleaved with NotI. It was purified again with the span column, so as to obtain a cDNA fragment.

(4) Expression Cloning

An EcoRI-NotI site was made in $pRSET_B$ (manufactured by Invitrogen), and the prepared cDNA was inserted into the site. Thereafter, the thus prepared vector was introduced into *Escherichia coli* JM109 DM3, followed by culture on an LA plate. Since a protein is synthesized in this strain, colonies that emit fluorescence when UV is applied were isolated.

As a result, 24 colonies emitting fluorescence were obtained from approximately 80,000 colonies. The nucleotide sequence thereof was determined with a DNA sequencer. This clone was named as Tanabe-Green. The amino acid sequence and nucleotide sequence of this clone are shown in SEQ ID NOS: 1 and 2, respectively.

Example 2

Analysis of Fluorescence Properties (1) Expression and Purification of Protein A BamHI site was added to the N-terminus of the obtained full-length cDNA, and an EcoRI site was added to the C-terminus thereof. Thereafter, it was subcloned in frame into $pRSET_B$ (manufactured by Invitrogen), and it was then expressed in *Escherichia coli* JM109 DE3. The expressed protein was purified with Ni-Agarose gel (manufactured by QIAGEN), utilizing an His-tag at the N-terminus thereof.

(2) Absorption Coefficient, Fluorescence and Excitation Spectra, and Quantum Yield The absorption spectrum of the fluorescent protein (Tanabe-Green) obtained in (1) above was measured using a 50 mM HEPES solution (pH 8.0). The molar absorption coefficient thereof was obtained from the protein concentration and the absorbance at the absorption maximum (494 nm). With regard to fluorescence and excitation spectra, using a 50 mM HEPES solution (pH 8.0), the fluorescence spectrum was measured by excitation at 470 nm, and the excitation spectrum was measured by fluorescence at 530 nm. The results are shown in FIG. 1. In addition, the quantum yield thereof was calculated based on the quantum yield of EGFP (manufactured by CLONTECH).

(3) Properties of pH Sensitivity

Figure 2:
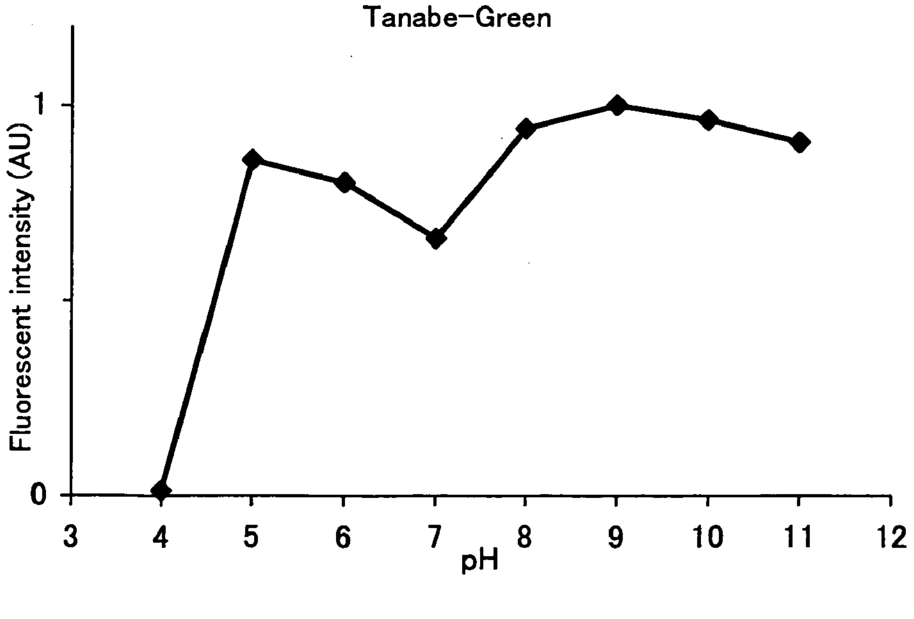
FIG. 2 shows pH sensitivity of Tanabe-Green.

The concentration of the protein was adjusted such that absorption at 470 nm became 0.01. Fluorescence intensity was measured (excitation: 470 nm; fluorescence: 506.5 nm) while the pH of the buffer was changed from pH 4 to pH 11. The results are shown in FIG. 2.

(4) Characteristics of Fluorescent Protein (Tanabe-Green)

The characteristics of the fluorescent protein (Tanabe-Green) including the fluorescence properties clarified by the measurements in (2) and (3) above are shown in the following Table 1:

TABLE 1

Fluorescence properties of Tanabe-Green

| Excitation maximum (nm) | Fluorescence maximum (nm) | Molar absorption coefficient ($M^{-1} \cdot cm^{-1}$) | Quantum Yield | PH sensitivity | Number of Amino acids | Expression in mammalian cells |
|---|---|---|---|---|---|---|
| 494 | 506 | 94,600 (494 nm, pH 8) | 0.65 | Non | 223 | Possible |

Example 3

Introduction of Fluorescent Protein (Tanabe-Green) Gene into Mammalian Cells A Tanabe-Green gene was introduced into HeLa cells using a LIPOFECTIN Reagent (Gibco), and it was introduced into rat hippocampal nerve cells by the calcium phosphate method.

Figure 3:
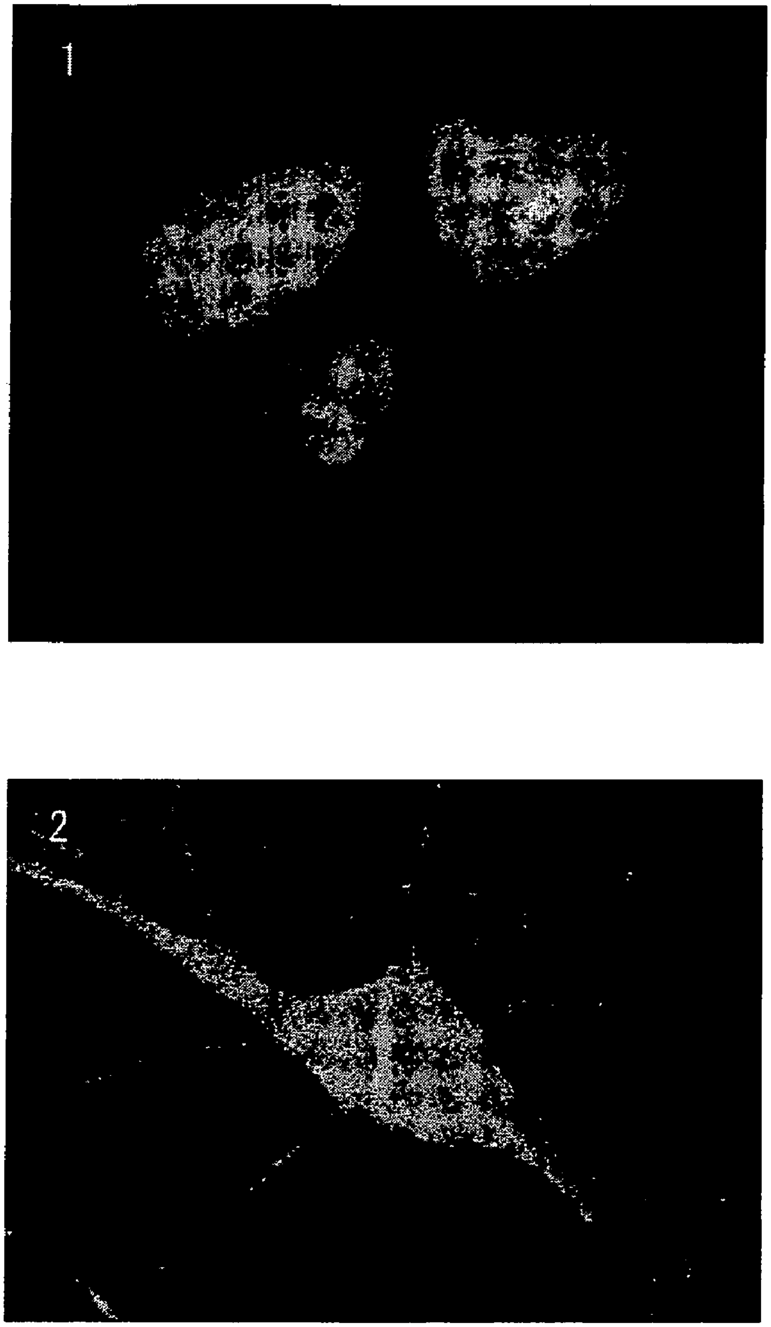
FIG. 3 shows the results obtained from introduction of a Tanabe-Green gene into mammalian cells. 1 represents the results of HeLa cells, and 2 represents those of rat hippocampal nerve cells.

Cells in which Tanabe-Green was expressed are shown in FIG. 3.

Example 4

Introduction of Mutation into Fluorescent Protein (Tanabe-Green) (I)

Mutations were introduced into the fluorescent protein (Tanabe-Green) by the following method.

(1) Random Mutagenesis

Using the cloned Tanabe-Green cDNA as a template, PCR was carried out in a state where $MnCl_2$ was added, so that mutations were randomly introduced.

TAKARA Taq (manufactured by Takara) was used as DNA polymerase. With regard to primers, a forward primer prepared by adding a BamHI site to the 5'-side and a reverse primer prepared by adding an EcoRI site to the 3'-side were used. The amplified DNA was cleaved with BamHI and EcoRI, and the obtained DNA fragment was inserted into $pRSET_B$. The obtained vector was introduced into *Escherichia coli* JM109 DM3, followed by culture on an LA plate. Thereafter, UV was applied onto the plate, and colonies that were likely to be mutated were isolated. The nucleotide sequence thereof was determined with a DNA sequencer.

Thus, a mutant (TG26) having reduced agglutinating properties, and a mutant (TG37) whose the peak of the fluorescence spectrum was shifted to a long wavelength and which had increased pH sensitivity were obtained. The amino acid sequence and nucleotide sequence of the mutant (TG26) are shown in SEQ ID NOS: 3 and 4, respectively. The amino acid sequence and nucleotide sequence of the mutant (TG37) are shown in SEQ ID NOS: 5 and 6, respectively.

Example 5

Analysis of Fluorescence Properties of Mutant Fluorescent Proteins (I)

(1) Expression and Purification of Proteins

A BamHI site was added to the N-terminus of the obtained full-length cDNA (of both TG26 and TG37), and an EcoRI site was added to the C-terminus thereof. Thereafter, it was subcloned in frame into $pRSET_B$ (manufactured by Invitrogen), and was then expressed in *Escherichia coli* JM109 DE3. The expressed protein was purified with Ni-Agarose gel (manufactured by QIAGEN), utilizing an His-tag at the N-terminus thereof.

Figure 4:
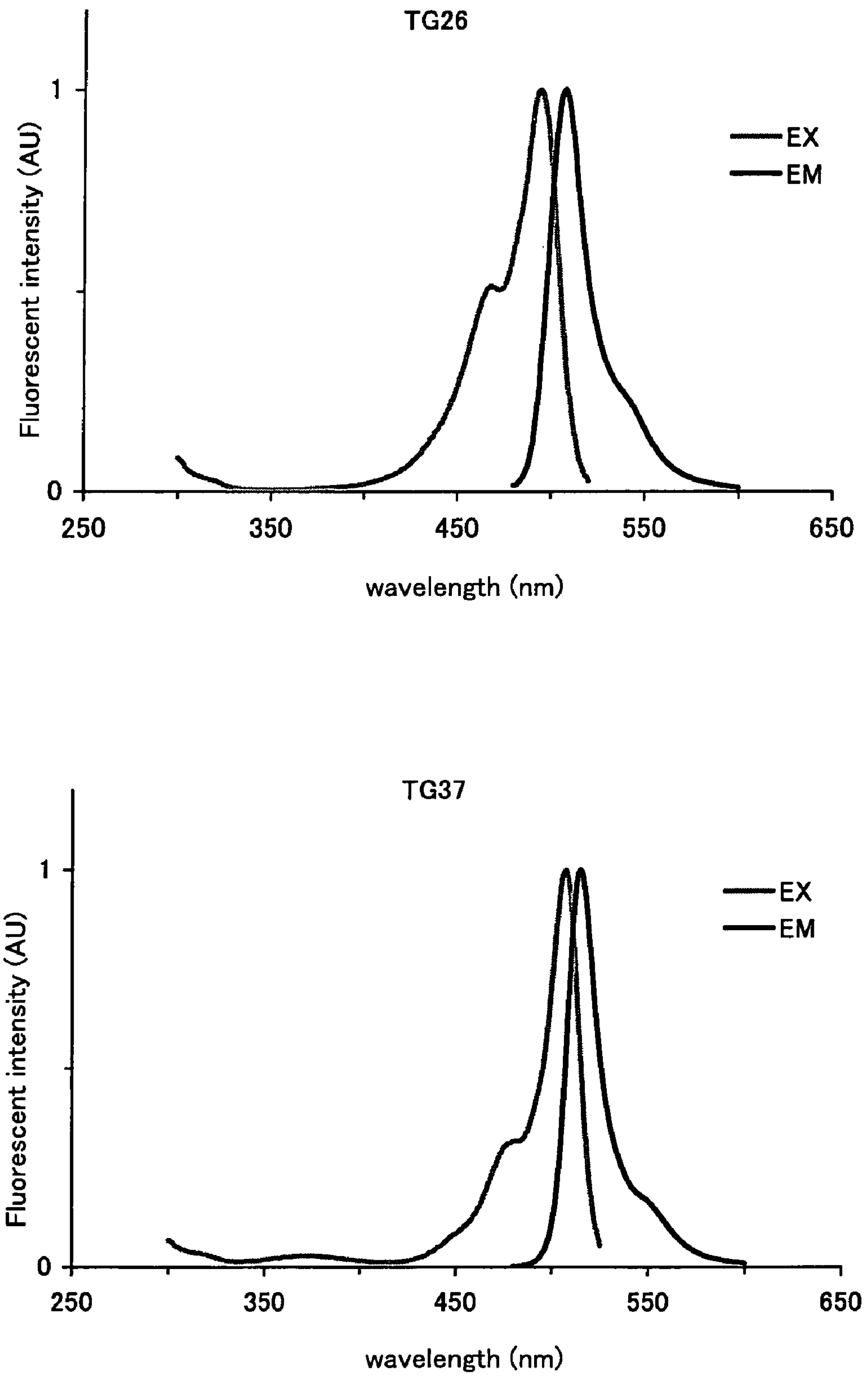
FIG. 4 shows excitation and fluorescence spectra of mutant proteins TG26 and TG37.

(2) Absorption Coefficient, Fluorescence and Excitation Spectra, and Quantum Yield The absorption spectrum of the mutant TG26 was measured using a 50 mM HEPES solution (pH 8.0). The molar absorption coefficient thereof was obtained from the protein concentration and the absorbance at the absorption maximum (494 nm). With regard to fluorescence and excitation spectra, using a 50 mM HEPES solution (pH 8.0), the fluorescence spectrum was measured by excitation at 470 nm, and the excitation spectrum was measured by fluorescence at 530 nm. The measurement results are shown in FIG. 4. In addition, the quantum yield thereof was calculated based on the quantum yield of EGFP (manufactured by CLONTECH).

The absorption spectrum of the mutant TG37 was measured using a 50 mM glycin solution (pH 10.0). The molar absorption coefficient thereof was obtained from the protein concentration and the absorbance at the absorption maximum (507 nm). With regard to fluorescence and excitation spectra, using a 50 mM glycin solution (pH 10.0), the fluorescence spectrum was measured by excitation at 470 nm, and the excitation spectrum was measured by fluorescence at 530 nm. The measurement results are shown in FIG. 4. In addition, the quantum yield thereof was calculated based on the quantum yield of EGFP (manufactured by CLONTECH).

(3) Properties of pH Sensitivity

Figure 5:
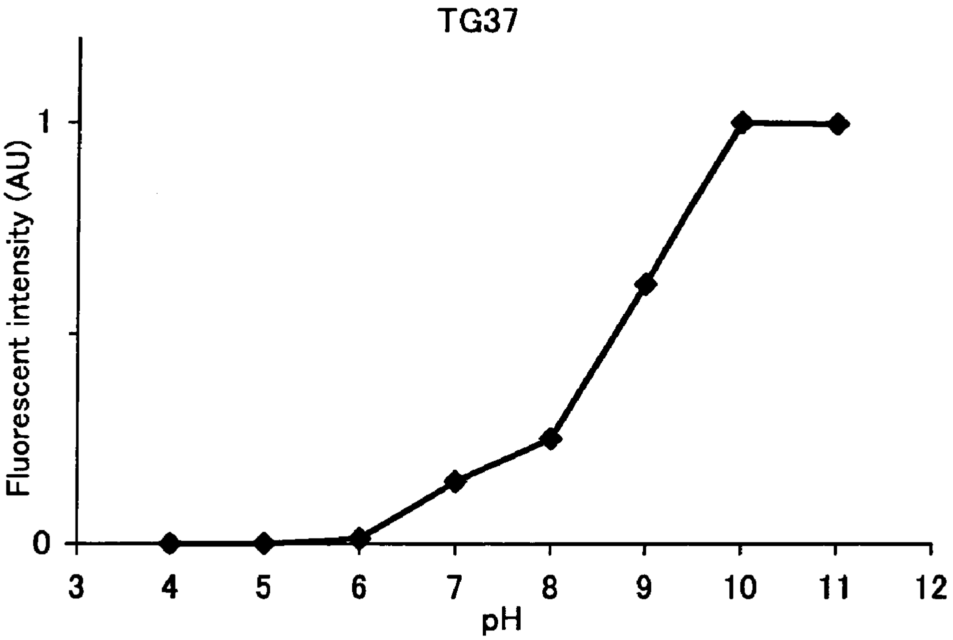
FIG. 5 shows pH sensitivity of the mutant proteins TG26 and TG37.
Figure 5:
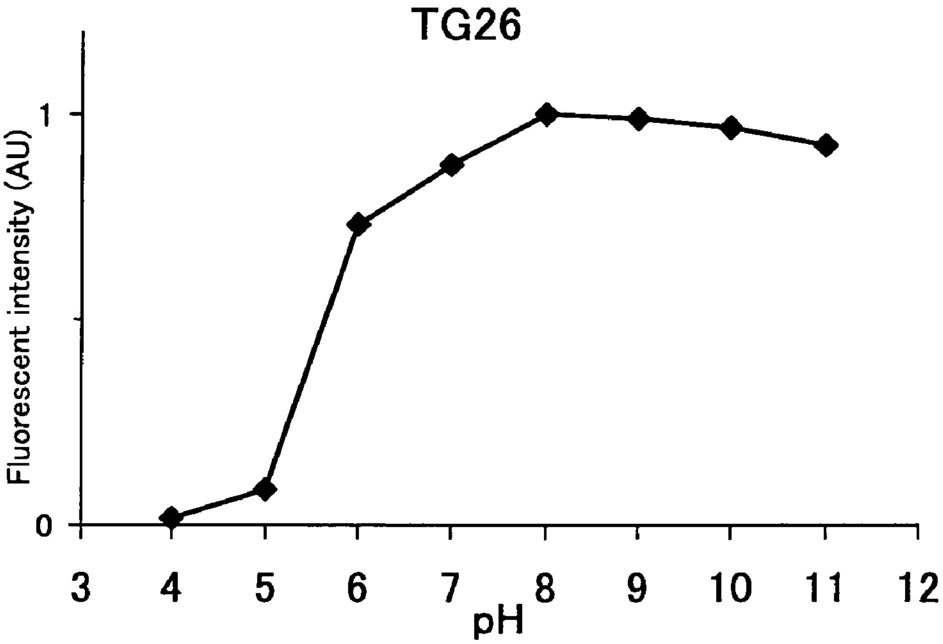

The concentration of the protein was adjusted such that absorption at 470 nm became 0.01. Fluorescence intensity was measured (excitation: 470 nm; fluorescence: 506.5 nm (for TG26) and 514.5 nm (for TG37)) while the pH of the buffer was changed from pH 4 to pH 11. The results are shown in FIG. 5.

(4) Characteristics of Mutant Fluorescent Proteins (TG26 and TG37)

The characteristics of the mutant fluorescent proteins (TG26 and TG37) including the fluorescence properties clarified by the measurements in (2) and (3) above are shown in the following Table 2:

TABLE 2

Fluorescence properties of TG26 and TG37

| Mutant | Excitation maximum (nm) | Fluorescence maximum (nm) | Molar absorption coefficient ($M^{-1} \cdot cm^{-1}$) | Quantum Yield | PH sensitivity | Number of amino acids | Expression in animal cells |
|---|---|---|---|---|---|---|---|
| TG26 | 494 | 507 | 68,800 (494 nm, pH 8) | 0.66 | pKa = 5.7 | 223 | Possible |
| TG37 | 507 | 514 | 88,600 (507 nm, pH 10) | 0.61 | pKa = 8.7 | 223 | Possible |

Example 6

Introduction of Mutation into Fluorescent Protein (Tanabe-Green) (II)

Mutations were introduced into the fluorescent protein (Tanabe-Green) by the following method.

(1) Random Mutagenesis

Using the cloned Tanabe-Green cDNA as a template, PCR was carried out in a state where $MnCl_2$ was added, so that mutations were randomly introduced.

TAKARA Taq (manufactured by Takara) was used as DNA polymerase. With regard to primers, a forward primer prepared by adding a BamHI site to the 5'-side and a reverse primer prepared by adding an EcoRI site to the 3'-side were used. The amplified DNA was cleaved with BamHI and EcoRI, and the obtained DNA fragment was inserted into $pRSET_B$. The obtained vector was introduced into *Escherichia coli* JM109 DM3, followed by culture on an LA plate. Thereafter, UV irradiation was applied onto the plate, and colonies that were likely to be mutated were isolated. The nucleotide sequence thereof was determined with a DNA sequencer.

Thus, a mutant (TGuv) whose the peak of the excitation spectrum was shifted to a short wavelength was obtained. The amino acid sequence and nucleotide sequence of the mutant (TGuv) are shown in SEQ ID NOS: 7 and 8, respectively.

Example 7

Analysis of Fluorescence Properties of Mutant Fluorescent Protein (II)

(1) Expression and Purification of Protein

A BamHI site was added to the N-terminus of the obtained full-length cDNA (TGuv), and an EcoRI site was added to the C-terminus thereof. Thereafter, it was subcloned in frame into $pRSET_B$ (manufactured by Invitrogen), and it was then expressed in *Escherichia coli* JM109 DE3. The expressed protein was purified with Ni-Agarose gel (manufactured by QIAGEN), utilizing an His-tag at the N-terminus thereof.

Figure 6:
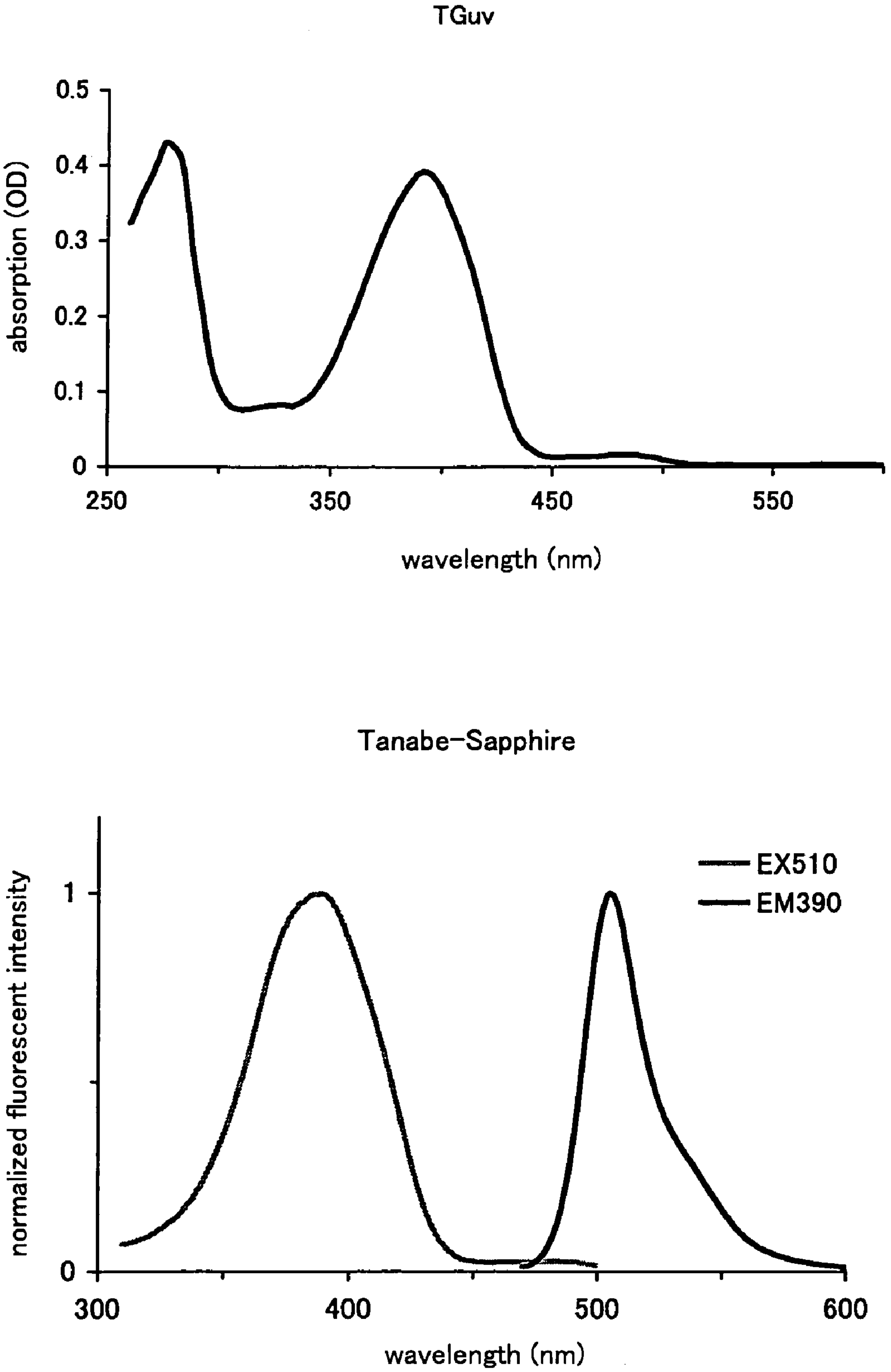
FIG. 6 shows excitation and fluorescence spectra of the mutant protein TGuv.
Figure 7:
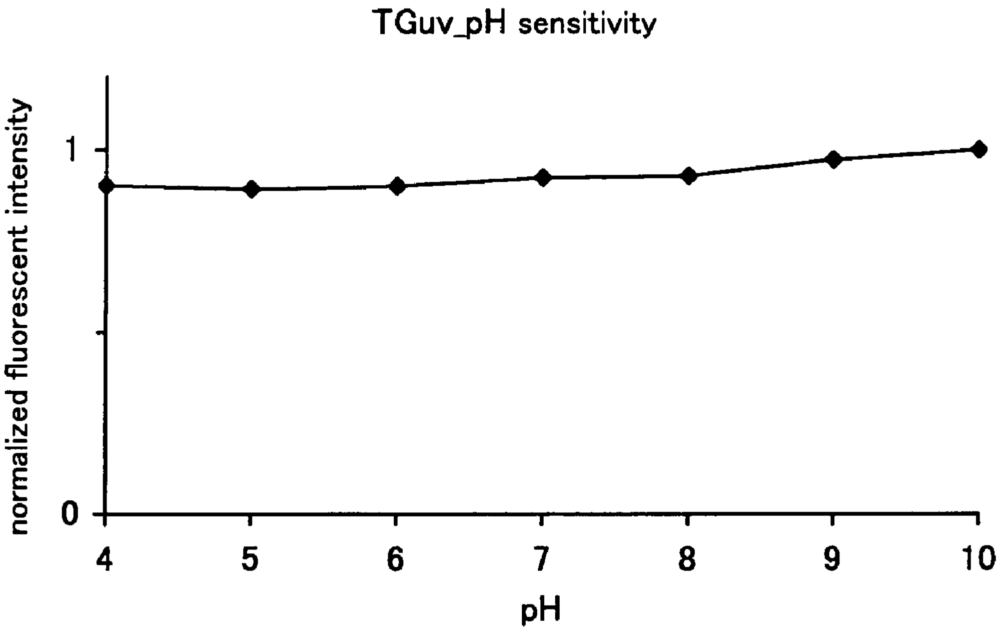
FIG. 7 shows pH sensitivity of the mutant protein TGuv.

(2) Absorption Coefficient, Fluorescence and Excitation Spectra, and Quantum Yield The absorption spectrum of the mutant TGuv was measured using a 50 mM HEPES solution (pH 7.5). The molar absorption coefficient thereof was obtained from the protein concentration and the absorbance at the absorption maximum (391 nm). With regard to fluorescence and excitation spectra, using a 50 mM HEPES solution (pH 7.5), the fluorescence spectrum was measured by excitation at 390 nm, and the excitation spectrum was measured by fluorescence at 510 nm. The measurement results are shown in FIG. 6. In addition, the quantum yield thereof was calculated based on the quantum yield of EGFP (manufactured by CLONTECH).

(3) Properties of pH Sensitivity

The concentration of the mutant protein TGuv was adjusted such that absorption at 391 nm became 0.01. Thereafter, fluorescence intensity at 505 nm was measured by excitation at 391 nm, using the following buffers:

pH 4 and 5: 50 mM AcONa-AcOH
pH 6: 50 mM MES-MaOH
pH 7: 50 mM MOPS-KOH
pH 8: 50 mM HEPES-NaOH
pH 9 and 10: 50 mM glycin-NaOH The results are shown in FIG. 6.

(4) Characteristics of Mutant Fluorescent Protein (TGuv)

The characteristics of the mutant fluorescent protein (TGuv) including the fluorescence properties clarified by the measurements in (2) and (3) above are shown in the following Table 3:

TABLE 3

| | Fluorescence properties of TGuv | | | | | | |
|---|---|---|---|---|---|---|---|
| Mutant | Excitation maximum (nm) | Fluorescence maximum (nm) | Molar absorption coefficient ($M^{-1} \cdot cm^{-1}$) | Quantum yield | PH sensitivity | Number of amino acids | Expression in animal cells |
| E140Q V157D F173V | 391 | 505 | 20,000 (391 nm, pH 7.5) | 0.84 | Non | 223 | Possible |

INDUSTRIAL APPLICABILITY

The present invention provides a novel fluorescent protein derived from sea anemone. The use of the fluorescent protein of the present invention enables fluorescent labeling of mammalian cells, and in particular, mammalian nerve cells, without exhibiting toxicity. Moreover, the use of a gene encoding the fluorescent protein of the present invention as a starting material provides the possibility of obtaining various fluorescent proteins having many different properties.

The invention claimed is:

1. An isolated DNA of any one of the following:

(a) DNA which encodes the amino acid sequence shown in SEQ ID NO: 1;

(b) DNA which encodes an amino acid sequence comprising a deletion, substitution and/or addition of one to five amino acids with respect to the amino acid sequence shown in SEQ ID NO: 1, and which encodes a fluorescent protein;

(c) DNA comprising a nucleotide sequence shown in SEQ ID NO: 2; or (d) DNA comprising a nucleotide sequence comprising a deletion, substitution and/or addition of one to fifteen nucleotides with respect to the nucleotide sequence shown in SEQ ID NO: 2, and encoding a fluorescent protein;

wherein the fluorescent protein has an excitation maximum wavelength between 391-507 nm and a fluorescence maximum wavelength between 505-514 nm.

2. An isolated DNA of any one of the following:

(a) DNA which encodes the amino acid sequence shown in SEQ ID NO: 3;

(b) DNA which encodes an amino acid sequence comprising a deletion, substitution and/or addition of one to five amino acids with respect to the amino acid sequence shown in SEQ ID NO: 3, and which encodes a fluorescent protein;

(c) DNA comprising a nucleotide sequence shown in SEQ ID NO: 4; or (d) DNA comprising a nucleotide sequence comprising a deletion, substitution, and/or addition of one to fifteen nucleotides with respect to the nucleotide sequence shown in SEQ ID NO: 4, and encoding a fluorescent protein;

wherein the fluorescent protein has an excitation maximum wavelength between 391-507 nm and a fluorescence maximum wavelength between 505-514 nm.

3. An isolated DNA of any one of the following:

(a) DNA which encodes the amino acid sequence shown in SEQ ID NO: 5;

(b) DNA which encodes an amino acid sequence comprising a deletion, substitution and/or addition of one to five amino acids with respect to the amino acid sequence shown in SEQ ID NO: 5, and which encodes a fluorescent protein;

(c) DNA comprising a nucleotide sequence shown in SEQ ID NO: 6; or (d) DNA comprising a nucleotide sequence comprising a deletion, substitution and/or addition of one to fifteen nucleotides with respect to the nucleotide sequence shown in SEQ ID NO: 6, and encoding a fluorescent protein;

wherein the fluorescent protein has an excitation maximum wavelength between 391-507 nm and a fluorescence maximum wavelength between 505-514 nm.

4. An isolated DNA of any one of the following:

(a) DNA which encodes the amino acid sequence shown in SEQ ID NO: 7;

(b) DNA which encodes an amino acid sequence comprising a deletion, substitution and/or addition of one to five amino acids with respect to the amino acid sequence shown in SEQ ID NO: 7, and which encodes a fluorescent protein;

(c) DNA comprising a nucleotide sequence shown in SEQ ID NO: 8; or (d) DNA comprising a nucleotide sequence comprising a deletion, substitution and/or addition of one to fifteen nucleotides with respect to the nucleotide sequence shown in SEQ ID NO: 8, and encoding a fluorescent protein;

wherein the fluorescent protein has an excitation maximum wavelength between 391-507 nm and a fluorescence maximum wavelength between 505-514 nm.

5. A recombinant vector having the DNA of claim 1.

6. An isolated transformant having the DNA of claim 1 or a recombinant vector comprising said DNA.

7. A fluorescent reagent kit which comprises at least one of: a) the DNA of SEQ ID NO: 2, b) a recombinant vector having the DNA of SEQ ID NO: 2, and c) an isolated transformant having the DNA of SEQ ID NO: 2.

8. The isolated DNA of claim 1, which encodes an amino acid sequence comprising a deletion, substitution and/or addition of one to five amino acids with respect to the amino acid sequence shown in SEQ ID NO: 1, said encoded amino acid sequence exhibiting fluorescent properties and having an excitation maximum wavelength between 391-507 nm and a fluorescence maximum wavelength between 505-514 nm.

9. The isolated DNA of claim 1, comprising a nucleotide sequence comprising a deletion, substitution and/or addition of one to fifteen nucleotides with respect to the nucleotide sequence shown in SEQ ID NO: 2, and encoding a fluorescent protein having an excitation maximum wavelength between 391-507 nm and a fluorescence maximum wavelength between 505-514 nm.

* * * * *

SEQUENCE LISTING

```
<160> NUMBER OF SEQ ID NOS: 8

<210> SEQ ID NO 1
<211> LENGTH: 223
<212> TYPE: PRT
<213> ORGANISM: Halcurias sp. L

<400> SEQUENCE: 1

Met Ser Val Ile Gly Lys Asp Met Ile Met Lys Leu His Val Glu Gly
1               5                   10                  15

Cys Val Asn Gly His Ser Phe Lys Ile Glu Gly Asp Gly Lys Gly Lys
            20                  25                  30

Pro Tyr Glu Gly Asp Gln Thr Val Lys Leu Arg Val Thr Glu Gly Gly
        35                  40                  45

Pro Leu Pro Phe Ala Phe Asp Ile Leu Ser Ala Ser Met Cys Tyr Gly
    50                  55                  60

Asn Arg Cys Phe Thr Lys Tyr Pro Ala Glu Ile Pro Asp Ile Phe Lys
65                  70                  75                  80

Gln Thr Phe Pro Glu Gly Tyr Ser Trp Glu Arg Ala Leu Thr Phe Glu
                85                  90                  95

Asp Gly Gly Phe Ala Ser Ser Ser Ser His Ile Ser Val Arg Gly Asn
            100                 105                 110

Cys Phe Phe Tyr Asp Val Lys Tyr His Gly Val Asn Phe Pro Ser Asn
        115                 120                 125

Gly Pro Ile Met Gln Arg Lys Thr Ile Gly Trp Glu Pro Ser Thr Glu
    130                 135                 140

Lys Leu Tyr Ile Gly Glu Gly Thr Leu Lys Gly Asp Val Thr Met Phe
145                 150                 155                 160

Leu Lys Leu Glu Gly Gly Gly Thr His Lys Cys His Phe Leu Thr Thr
                165                 170                 175

Tyr Lys Thr Lys Lys Asp Val Gln Met Pro Asp Ser His Phe Ile Asp
            180                 185                 190

His Arg Leu Leu Thr Ser His Leu Asp Lys Glu Cys Asn Asn Val Glu
        195                 200                 205

Leu Arg Glu His Ala Val Ala Arg Asn Ser Ser Leu Pro Ser Arg
    210                 215                 220


<210> SEQ ID NO 2
<211> LENGTH: 672
<212> TYPE: DNA
<213> ORGANISM: Halcurias sp. L

<400> SEQUENCE: 2

atgagtgtta ttggaaaaga catgataatg aaattgcatg tggaaggatg tgtcaacggc      60

cactccttca agattgaggg tgacggcaaa ggcaaaccgt acgagggaga ccaaactgtg     120

aagcttcgtg ttactgaagg agggccctta ccattcgcat ttgacatctt gtcagcctca     180

atgtgttatg gaaacaggtg ttttaccaaa tatccggcag agattcccga cattttcaag     240
```

-continued

```
cagacatttc ctgaaggcta ctcatgggaa agagccttga catttgaaga tggagggttt    300

gcttcatcaa gctcgcacat cagtgtccgt ggcaactgct tcttctacga cgtcaaatat    360

catggcgtaa acttcccttc caatggacca attatgcaaa gaaagacaat cggctgggaa    420

ccatccacag agaaattgta catcggagag ggaacgctga agggtgatgt tacgatgttc    480

ctcaagctcg aaggaggggg aactcataaa tgccacttcc taaccactta caaaacgaag    540

aaagatgtcc agatgccaga cagccacttc attgaccatc gtctcctgac cagccacctt    600

gataaggaat gcaacaacgt ggaattgcgc gagcatgcag ttgcgcgtaa ctcaagtctg    660

ccttcccgtt aa                                                        672
```

```
<210> SEQ ID NO 3
<211> LENGTH: 223
<212> TYPE: PRT
<213> ORGANISM: Halcurias sp. L

<400> SEQUENCE: 3

Met Ser Val Ile Gly Lys Asp Met Ile Met Lys Leu His Val Glu Gly
1               5                   10                  15

Cys Val Asn Gly His Ser Phe Lys Ile Glu Gly Asp Gly Asn Gly Lys
            20                  25                  30

Pro Tyr Glu Gly Asp Gln Thr Val Lys Leu Arg Val Thr Glu Gly Gly
        35                  40                  45

Pro Leu Pro Phe Ala Phe Asp Ile Leu Ser Ala Ser Met Cys Tyr Gly
    50                  55                  60

Asn Arg Cys Phe Thr Lys Tyr Pro Ala Glu Ile Pro Asp Ile Phe Lys
65                  70                  75                  80

Gln Thr Phe Pro Glu Gly Tyr Ser Trp Glu Arg Ala Leu Thr Phe Glu
                85                  90                  95

Asp Gly Gly Phe Ala Ser Ser Ser Ser His Ile Ser Val Arg Gly Asn
            100                 105                 110

Cys Phe Phe Tyr Asp Val Lys Tyr His Gly Val Asn Phe Pro Ser Asn
        115                 120                 125

Gly Pro Ile Met Gln Arg Lys Thr Ile Gly Trp Glu Pro Ser Thr Glu
    130                 135                 140

Lys Leu Tyr Phe Gly Glu Gly Thr Leu Lys Gly Asp Val Thr Met Phe
145                 150                 155                 160

Leu Lys Leu Glu Gly Gly Gly Thr His Arg Cys His Phe Gln Thr Thr
                165                 170                 175

Tyr Lys Thr Lys Lys Asp Val Gln Met Pro Asp Ser His Phe Ile Asp
            180                 185                 190

His Arg Leu Leu Thr Ser His Leu Asp Lys Glu Ser Asn Asn Val Glu
        195                 200                 205

Leu Arg Glu His Ala Val Ala Arg Asn Ser Ser Leu Pro Ser Arg
    210                 215                 220
```

```
<210> SEQ ID NO 4
<211> LENGTH: 672
<212> TYPE: DNA
<213> ORGANISM: Halcurias sp. L

<400> SEQUENCE: 4

atgagtgtta ttggaaaaga catgataatg aaattgcatg tggaaggatg tgtcaacggc     60

cactccttca agattgaggg tgacggcaat ggcaaaccgt acgagggtga ccaaactgtc    120

aagcttcgtg ttactgaagg agggccctta ccattcgcat ttgacatctt gtcagcctca    180
```

-continued

```
atgtgttatg gaaacaggtg ttttaccaaa tatccggcag agattcccga cattttcaag    240

cagacatttc ctgaaggcta ctcatgggaa agagccttga catttgagga tggagggttt    300

gcttcatcaa gctcgcacat cagtgtccgt ggcaactgct tcttctacga cgtcaaatat    360

catggcgtaa acttcccttc caatggacca attatgcaaa gaaagacaat cggctgggaa    420

ccatccacag agaaattgta cttcggagag ggaacgctga agggtgatgt tacgatgttc    480

ctcaagctcg aaggaggggg aacccataga tgccacttcc aaaccactta caaaacgaag    540

aaagatgtcc agatgccaga cagccacttc attgaccatc gtctcctgac cagccacctt    600

gataaggaat ccaacaacgt ggaattgcgc gagcacgcag ttgcgcgtaa ctcaagtctg    660

ccttcccgtt aa                                                         672
```

<210> SEQ ID NO 5
<211> LENGTH: 223
<212> TYPE: PRT
<213> ORGANISM: Halcurias sp. L

<400> SEQUENCE: 5

```
Met Ser Val Ile Gly Lys Asp Met Ile Met Lys Leu His Val Glu Gly
1               5                   10                  15

Cys Val Asn Gly His Ser Phe Lys Ile Glu Gly Asp Gly Lys Gly Lys
            20                  25                  30

Pro Tyr Glu Gly Asp Gln Thr Val Lys Leu Arg Val Thr Glu Gly Gly
        35                  40                  45

Pro Leu Pro Phe Ala Phe Asp Ile Leu Ser Ala Ser Met Cys Tyr Gly
    50                  55                  60

Asn Arg Cys Phe Thr Lys Tyr Pro Ala Glu Ile Pro Asp Ile Phe Lys
65                  70                  75                  80

Gln Thr Phe Pro Glu Gly Tyr Ser Trp Glu Arg Ala Leu Thr Phe Glu
                85                  90                  95

Asp Gly Gly Phe Ala Ser Ser Ser Ser His Ile Ser Val Arg Gly Asn
            100                 105                 110

Cys Phe Phe Tyr Asp Val Lys Tyr His Gly Val Asn Phe Pro Ser Asn
        115                 120                 125

Gly Pro Ile Met Gln Arg Lys Thr Ile Gly Trp Glu Pro Ala Thr Glu
    130                 135                 140

Lys Leu Tyr Ile Gly Glu Gly Thr Leu Lys Gly Asp Val Thr Met Phe
145                 150                 155                 160

Leu Lys Leu Glu Gly Gly Gly Thr His Lys Cys His Phe Leu Thr Thr
                165                 170                 175

Tyr Lys Thr Lys Lys Asp Val Gln Met Pro Asp Ser His Phe Ile Asp
            180                 185                 190

His Arg Leu Leu Thr Ser His Leu Asp Lys Glu Cys Asn Asn Val Glu
        195                 200                 205

Leu Arg Glu His Ala Val Ala Arg Asn Ser Ser Leu Pro Ser Arg
    210                 215                 220
```

<210> SEQ ID NO 6
<211> LENGTH: 672
<212> TYPE: DNA
<213> ORGANISM: Halcurias sp. L

<400> SEQUENCE: 6

```
atgagtgtta ttggaaaaga catgataatg aaattgcatg tggaaggatg tgtcaacggc     60
```

-continued

```
cactccttca agattgaggg tgacggcaaa ggcaaaccgt acgagggaga ccaaactgtg    120

aagcttcgtg ttactgaagg agggccctta ccattcgcat ttgacatctt gtcagcctca    180

atgtgttatg gaaacaggtg ttttaccaaa tatccggcag agattcccga cattttcaag    240

cagacatttc ctgaaggcta ctcatgggaa agagccttga catttgaaga tggagggttt    300

gcttcatcaa gctcgcacat cagtgtccgt ggcaactgct tcttctacga cgtcaaatat    360

catggcgtaa acttcccttc caatggacca attatgcaaa gaaagacaat cggctgggaa    420

ccagccacag agaaattgta catcggagag ggaacgctga agggtgatgt tacgatgttc    480

ctcaagctcg aaggaggggg aactcataaa tgccacttcc taaccactta caaaacgaag    540

aaagatgtcc agatgccaga cagccacttc attgaccatc gtctcctgac cagccacctt    600

gataaggaat gcaacaacgt ggaattgcgc gagcatgcag ttgcgcgtaa ctcaagtctg    660

ccttcccgtt aa                                                        672
```

```
<210> SEQ ID NO 7
<211> LENGTH: 223
<212> TYPE: PRT
<213> ORGANISM: Halcurias sp. L

<400> SEQUENCE: 7

Met Ser Val Ile Gly Lys Asp Met Ile Met Lys Leu His Val Glu Gly
1               5                   10                  15

Cys Val Asn Gly His Ser Phe Lys Ile Glu Gly Asp Gly Lys Gly Lys
            20                  25                  30

Pro Tyr Glu Gly Asp Gln Thr Val Lys Leu Arg Val Thr Glu Gly Gly
        35                  40                  45

Pro Leu Pro Phe Ala Phe Asp Ile Leu Ser Ala Ser Met Cys Tyr Gly
    50                  55                  60

Asn Arg Cys Phe Thr Lys Tyr Pro Ala Glu Ile Pro Asp Ile Phe Lys
65                  70                  75                  80

Gln Thr Phe Pro Glu Gly Tyr Ser Trp Glu Arg Ala Leu Thr Phe Glu
                85                  90                  95

Asp Gly Gly Phe Ala Ser Ser Ser Ser His Ile Ser Val Arg Gly Asn
            100                 105                 110

Cys Phe Phe Tyr Asp Val Lys Tyr His Gly Val Asn Phe Pro Ser Asn
        115                 120                 125

Gly Pro Ile Met Gln Arg Lys Thr Ile Gly Trp Gln Pro Ser Thr Glu
    130                 135                 140

Lys Leu Tyr Ile Gly Glu Gly Thr Leu Lys Gly Asp Asp Thr Met Phe
145                 150                 155                 160

Leu Lys Leu Glu Gly Gly Gly Thr His Lys Cys His Val Leu Thr Thr
                165                 170                 175

Tyr Lys Thr Lys Lys Asp Val Gln Met Pro Asp Ser His Phe Ile Asp
            180                 185                 190

His Arg Leu Leu Thr Ser His Leu Asp Lys Glu Cys Asn Asn Val Glu
        195                 200                 205

Leu Arg Glu His Ala Val Ala Arg Asn Ser Ser Leu Pro Ser Arg
    210                 215                 220
```

```
<210> SEQ ID NO 8
<211> LENGTH: 672
<212> TYPE: DNA
<213> ORGANISM: Halcurias sp. L

<400> SEQUENCE: 8
```

-continued

```
atgagtgtta ttggaaaaga catgataatg aaattgcatg tggaaggatg tgtcaacggc     60
cactccttca agattgaggg tgacggcaaa ggcaaaccgt acgagggaga ccaaactgtg    120
aagcttcgtg ttactgaagg agggccctta ccattcgcat ttgacatctt gtcagcctca    180
atgtgttatg gaaacaggtg ttttaccaaa tatccggcag agattcccga cattttcaag    240
cagacatttc ctgaaggcta ctcatgggaa agagccttga catttgaaga tggagggttt    300
gcttcatcaa gctcgcacat cagtgtccgt ggcaactgct tcttctacga cgtcaaatat    360
catggcgtaa acttcccttc caatggacca attatgcaaa gaaagacaat cggctggcaa    420
ccatccacag agaaattgta catcggagag ggaacgctga agggtgatga tacgatgttc    480
ctcaagctcg aaggaggggg aactcataaa tgccacgtcc taaccactta caaaacgaag    540
aaagatgtcc agatgccaga cagccacttc attgaccatc gtctcctgac cagccacctt    600
gataaggaat gcaacaacgt ggaattgcgc gagcatgcag ttgcgcgtaa ctcaagtctg    660
ccttcccgtt aa                                                        672
```